United States Patent [19]

Okabe et al.

[11] Patent Number: 4,856,353

[45] Date of Patent: Aug. 15, 1989

[54] NONDESTRUCTIVE INSPECTION APPARATUS FOR HEAT-TRANSFER TUBES IN BOILERS

[75] Inventors: Yoshimi Okabe; Katsumi Kikuchi, both of Tokyo, Japan

[73] Assignees: The Tokyo Electric Power Co.; Ishikwajima-Harima Jukogyo Kabushiki Kaisha, both of Japan

[21] Appl. No.: 323,192

[22] Filed: Mar. 13, 1989

Related U.S. Application Data

[63] Continuation-in-part of Ser. No. 141,421, Jan. 7, 1988, abandoned.

[30] Foreign Application Priority Data

Jan. 30, 1987 [JP] Japan ................................. 62-20146

[51] Int. Cl.$^4$ .............................................. G02B 6/00
[52] U.S. Cl. .................................................. 73/865.8
[58] Field of Search ..................... 73/865.8, 866.5, 623; 350/96.23, 96.2, 96.1; 356/241, 138, 153

[56] References Cited

U.S. PATENT DOCUMENTS

| | | | |
|---|---|---|---|
| 3,481,660 | 12/1969 | Sheldon | 350/96.26 |
| 3,809,072 | 5/1974 | Ersek et al. | 350/96.26 |
| 4,273,109 | 6/1981 | Enderby | 350/96.26 |
| 4,398,796 | 8/1983 | Dalgoutte et al. | 350/96.2 |
| 4,597,294 | 7/1986 | Brill, III et al. | 73/623 |

FOREIGN PATENT DOCUMENTS

| | | | |
|---|---|---|---|
| 5149775 | 4/1976 | Japan . | |
| 0595861 | 2/1984 | Japan . | |
| 0266458 | 11/1987 | Japan | 73/865.9 |

*Primary Examiner*—Robert R. Raevis

[57] ABSTRACT

When a measuring instrument is inserted through a header into a boiler heat-transfer tube so as to carry out inspection, a guide for insertion of the measuring instrument is positively and correctly aligned with a heat transfer tube hole of the header.

3 Claims, 5 Drawing Sheets

NONDESTRUCTIVE INSPECTION APPARATUS FOR HEAT-TRANSFER TUBES IN BOILERS

This application is a continuation-in-part of application Ser. No. 07/141,421 filed Jan. 7, 1988, now abandoned.

BACKGROUND OF THE INVENTION

The present invention relates to a non-destructive inspection apparatus for heat-transfer tubes in boilers.

Heat-transfer tubes in boilers, which become thinner in thickness due to wear, corrosion and the like, are periodically inspected so as to measure the thickness of each heat-transfer tube.

To this end, conventionally a temporary scaffold is assembled in the boiler furnace upon inspection and an inspector stands on the scaffold to measure the thickness of each heat-transfer tube from exterior thereof.

The inspection system of this type has been proved to have the following problems:

(i) Since assembling a temporary scaffold is involved, inspection time becomes longer and inspection cost becomes expensive due to extra materials and labor required.

(ii) Inspection work is dangerous since an inspector must accomplish the inspection while standing on a temporary scaffold which is unstable.

(iii) Because of inspection in burnt-gas passages, inspection environment and efficiency are adversely affected by dust and the like accumulated.

To overcome these problems, there has been proposed a system in which, as shown in FIG. 1, an inspection hole 3 is formed through a side face of a header 2 for boiler heat-transfer tubes 1. Inserted through the hole 3 is a guide 4 through which in turn a wall-thickness measuring instrument 5 is inserted into the heat-transfer tube 1, thereby measuring the wall thickness of each heat-transfer tube 1 from interior thereof.

The measuring instrument 5 comprises a sensor 6 and a cable 8 having a plurality of spaced floats 7 and connected to the sensor 6. The measuring instrument 5 is introduced together with compressed fluid into the guide 4 so that the floats 7 behave like pistons, whereby the measuring instrument 5 is displaced.

Referring next to FIGS. 2-5, a leading portion of the guide 4 will be described. An outer guide pipe 10 having a two-piece type leading portion receives a slide frame 11 which has a two-piece type leading portion and which in turn receives in their leading portions a head 13 through a pin 14; the head 13 is provided for insertion of the measuring instrument 5 into the heat-transfer tube 1 as will be described hereinafter. The head 13 has an upper portion integrally formed with a lever 15 to which one end of a link 16 is pivotably connected with a pin. The other end of the link 16 is pivotably connected with a pin to a slide bar 17 which is slidably disposed along the slide frame 11 within the outer guide pipe 10 so that push or pull of the slide bar 17 causes the head 13 to rotate.

Furthermore, four supporting legs 19 each having a rotatable and swingable roller 18 at its leading end are pivoted in the form of a cross to a supporting-leg head 22 and are normally retained open or divergent by means of a cylindrical member 21 which is loaded with a spring 20 (see FIG. 2). Slide beams 23 are securely attached to the head 22 through bolting or the like to sandwich the same and are slidably inserted between the outer guide pipe 10 and the slide frame 11 so that the head 13 is adapted to be received between the slide beams 23 when the supporting-leg head 22 is displaced away from the head 13.

As best shown in FIG. 5, a movable head 25 is slidably fitted into a space 24 defined within the head 13. A flexible tube (vinyl tube) 26 extends through the outer guide pipe 10 and is connected to the head 13 such that one end of the tube 26 is opened at the space 24. A tension spring 27 is loaded in the head 13 to pull the movable head 25 in the direction away from the inner surface of the header 2. An annular spacer 28 is securely interposed between the end of the flexible tube 26 and the movable head 25 in the space 24. Stoppers (not shown) are disposed such that a pressure-receiving surface of the movable head 25 and the spacer 28 are not made in contact with each other and therefore a minimum space or gap 29 is maintained between them.

An end of the guide 4 away from the head 13 has bolt holes 30 each for locking of the corresponding slide frame 11 and slide beam 23 together.

Upon measurement of the wall thickness, first the guide 4 is inserted through the inspection hole 3 at one end face of the header 2. More particularly, an inspector inserts the leading end of the guide 4 into the header 2 through the inspection hole 3 with the supporting legs 19 being manually closed or converged. Then, the inspector manually releases the supporting legs 19 to open, whereby the latter are pushed by the cylindrical member 21 under the force of the spring 20 so that a rotating surface of each roller 18 is pressed against the inner surface of the header 2 to support the guide 4. In this case, the supporting-leg head 22 is away from the head 13 so that the head 13 is being received between the slide beams 23 to be aligned with the outer guide pipe 10. Then, pushing the slide bar 17 toward the head 13 forces the lever 15 to move to an upright position through the link 16; that is, the head 13 is rotated about the pin 14 through a right angle. In this rotation, a leading portion of the flexible tube 26 which has been straight is easily bent. Thereafter, the slide beam 23 is pulled to the right in FIG. 2 so that the supporting-leg head 22 is retracted and abuts on the head 13. Bolts are screwed into the bolt holes 30 to lock the slide frame 11 with the slide beams to thereby securely hold the head 13.

After the head 13 is securely held in this manner, the position of the guide 4 is so adjusted that the movable head 25 in the head 13 is aligned with a heat-transfer-tube hole 12 of the header 2. Then, the sensor 6 and the cable 8 with the floats 7 are inserted into the flexible tube 26, utilizing the pressure of water. Therefore, as described previously, the floats 7 behave like pistons so that the measuring instrument 5 passes through the tube 26 and reaches the head 13.

When the sensor 6 and the float 7 at the leading end reach the head 13 and then pass into the movable head 25, the water pressure acts on the flanged pressure-receiving surface of the movable head 25 through the minimum space or gap 29. As a result, the movable head 25 is forced to move toward the hole 12 against the force of the tension spring 27 so that the movable head 25 is urged to contact the inner wall surface of the heat-transfer tube 1. Thus, the measuring instrument 5 is inserted into the heat-transfer tube 1 to measure the wall thickness thereof.

With the system of the type described just above, the movable head 25 is activated by water pressure so that there arises a problem that water may leak from the head 13 into the header 2.

In order to overcome this problem, there has been proposed a system for positively pressing a pressure head formed integral with the flexible tube against the inner surface of the header, thereby maintaining sealability.

In either of the above-mentioned systems, accurate alignment of the leading end of the head 13 with the heat-transfer tube 1 in the header 2 is difficult to carry out. When the leading end of the head 13 is not correctly aligned with the hole 12, leakage of the compressed fluid and/or damage of the galled parts will result. In order to overcome this problem, there has been further proposed a system in which an optical fiber or the like is inserted into the flexible tube 26 so that an inspector can accomplish the alignment of the leading end of the head 13 with the heat-transfer-tube hole 12 while watching the latter.

Even in the last-mentioned system, it is difficult to confirm correct alignment of the leading end of the head with the hole 12 of the header 2.

In view of the above, a primary object of the present invention is to easily and positively confirm alignment of the leading end of the head with the heat-transfer tube, thereby improving inspection efficiency and preventing the above and other problems such as leakage of compressed fluid.

The present invention will become more apparent from the following description of a preferred embodiment thereof taken in conjunction with the accompanying drawings.

DETAILED DESCRIPTION OF THE PREFERRED EMBODIMENT

Figure 1:
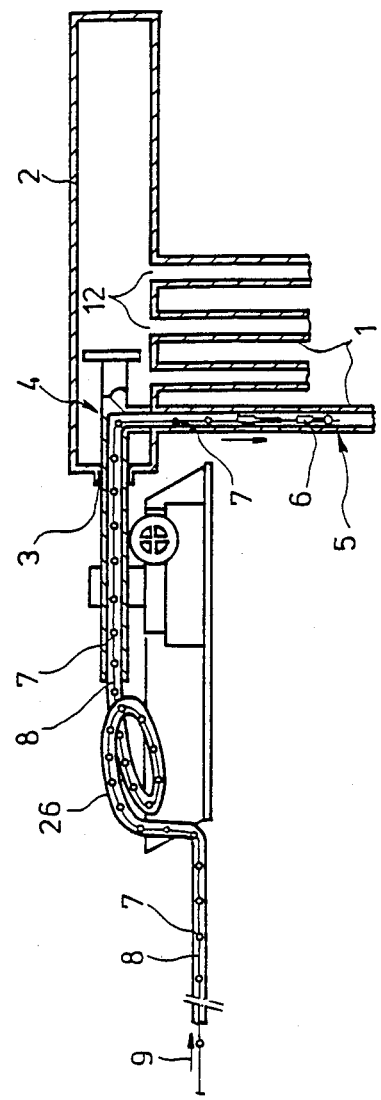
FIG. 1 is a view used to explain one example of conventional inspection apparatuses.

Referring to FIGS. 6–9, a preferred embodiment of the present invention will be described. The outer guide pipe 10 which provides the leading end of the guide 4 is axially notched over a predetermined length at its upper and lower portions to provide passages 31 and 32. The outer guide pipe 10 has, adjacent to the passages 31 and 32, axial slots to which a tiltable head 13 is pivoted with pins 14 (See FIG. 8) such that the head 13 and the lever 15 formed integral therewith are extruded out of the outer guide tube 10 through the passages 31 and 32 when they are brought to their upright position. The head 13 supports therein a rotatable threaded shaft 33 such that when the head 13 and the lever 15 are in the upright position, the threaded shaft 33 is directed vertically. The shaft 33 is threadably engaged at its lower portion with an internally threaded boss 34 which is supported by supporting means (not shown) such that the boss 34 can be displaced axially without rotation. Securely attached to an end of the boss 34 away from the shaft 33 is a tube guide 35 which is curved at a predetermined radius of curvature. A flexible tube (vinyl tube) 26 is inserted into the tube guide 35 and a leading end of the tube 26 is securely held in position by a locking flange 36 securely attached to the tube guide 35 and by a push flange 37 which has a rubber packing 38 bonded to a surface of the flange 37 near the inner surface of the header 2.

Figure 6:
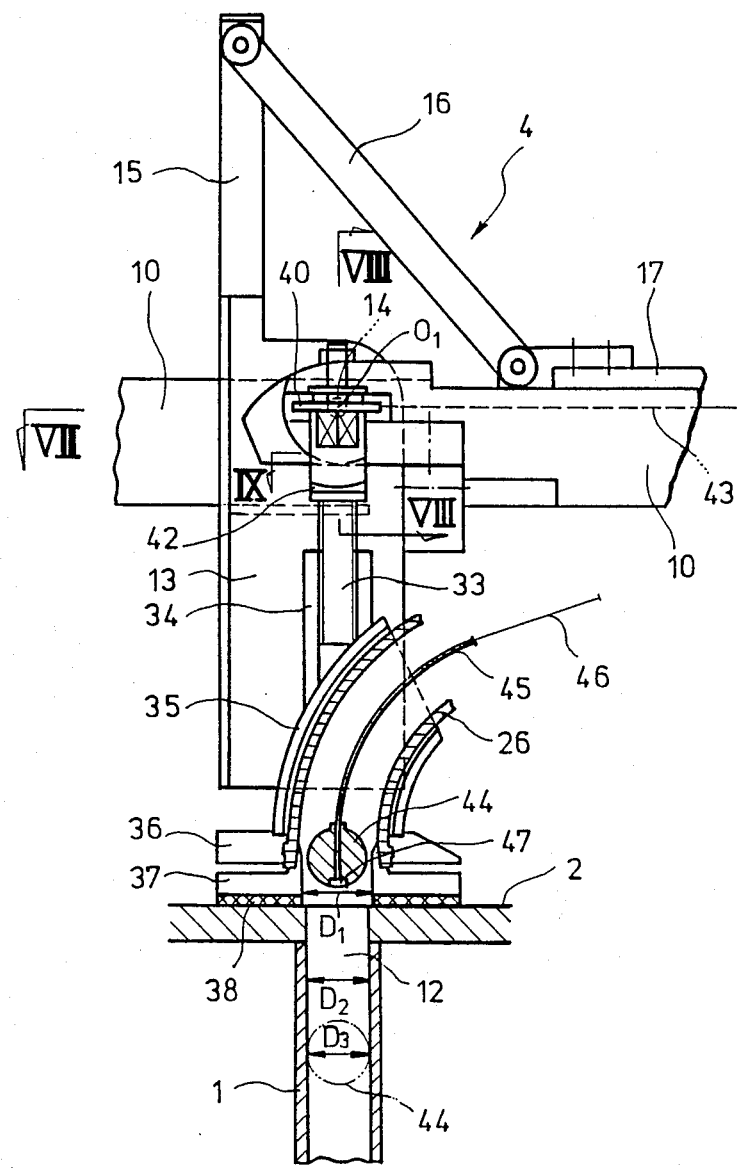
FIG. 6 is a sectional view used to explain a preferred embodiment of the present invention.
Figure 7:
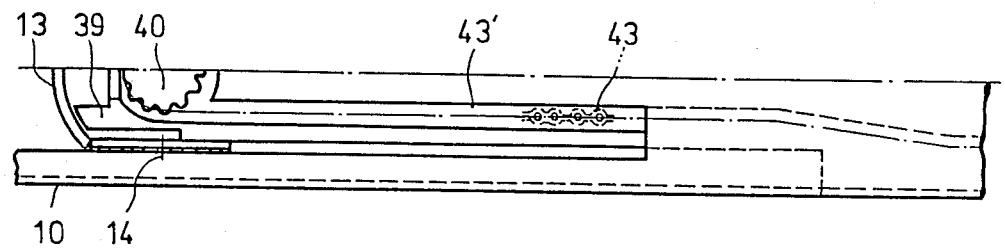
FIG. 7 is a sectional view taken along the line VII in FIG. 6.
Figure 8:
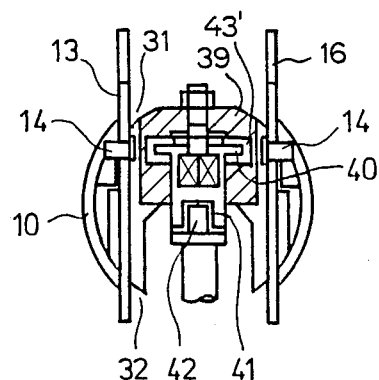
FIG. 8 is a sectional view taken along the line VIII in FIG. 6.

The outer guide pipe 10 receives axially slidably an inner guide pipe 39 so that the leading end of the pipe 39 near the head 13 can be displaced into the head 13. The leading end of the inner guide pipe 39 near the head 13 rotatably supports a vertically extending sprocket wheel 40 in position such that intersection $O_1$ of a sprocket wheel axis with a center plane of the sprocket wheel is aligned with the pins 14 as shown in FIG. 6 when the inner guide pipe 39 is moved to its forwardmost position.

Figure 9:
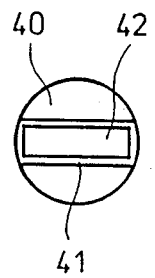
FIG. 9 is a sectional view taken along the line IX in FIG. 6.

As best shown in FIG. 9, the sprocket wheel 40 is formed at its boss portion with a groove 41 which extends in the axial direction of the inner guide pipe 39 and which opens downwardly. A flat projection 42 fixed on an end of the shaft 33 away from the guide 35 can be fitted into the groove 41 when the head 13 and the lever 15 are brought to the upright position. Reference numeral 43 represents a chain; and 43', a chain groove.

Figure 2:
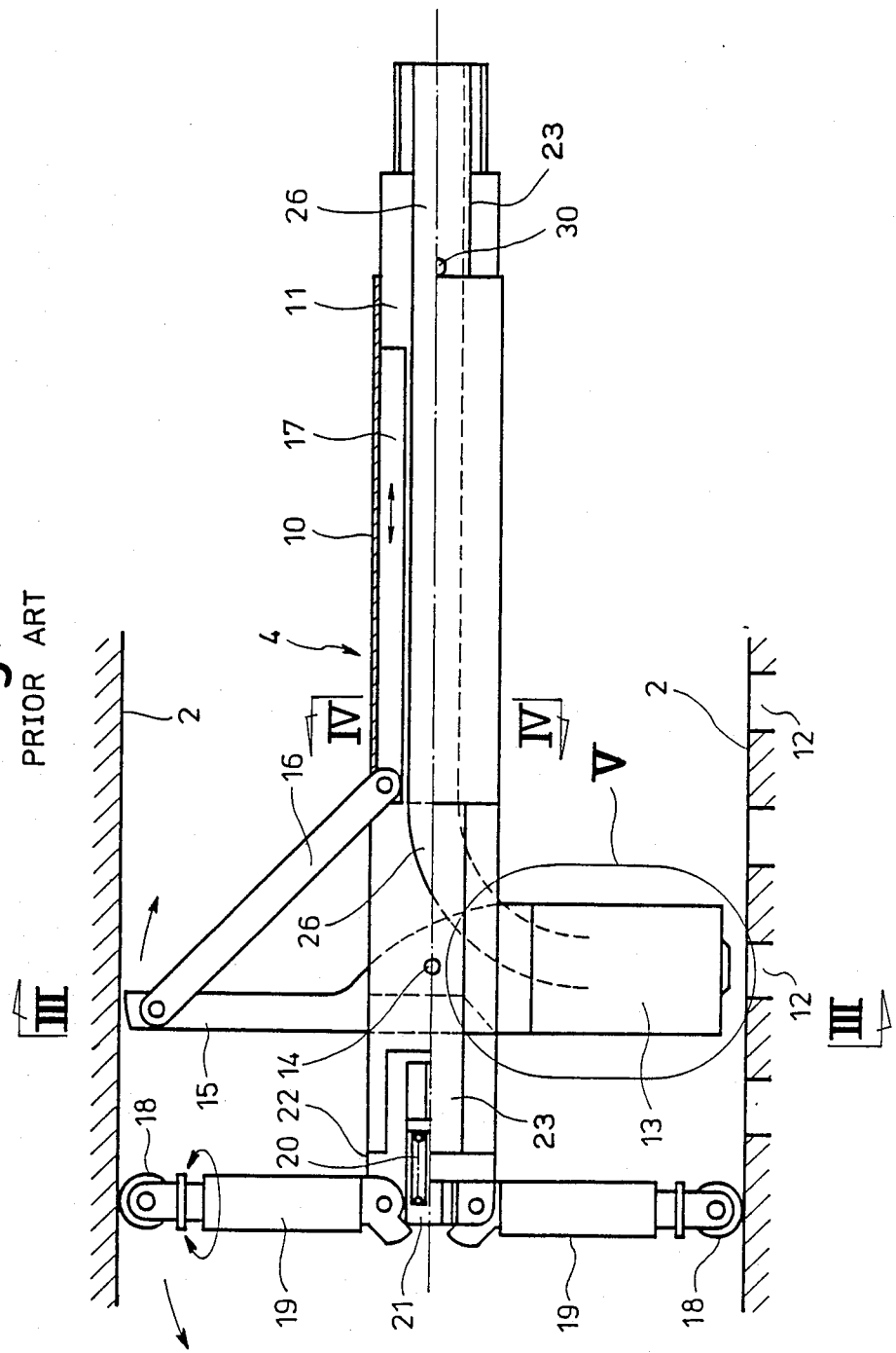
FIG. 2 is a detailed view used to explain one example of conventional guides used in the conventional inspection apparatuses.
Figure 3:
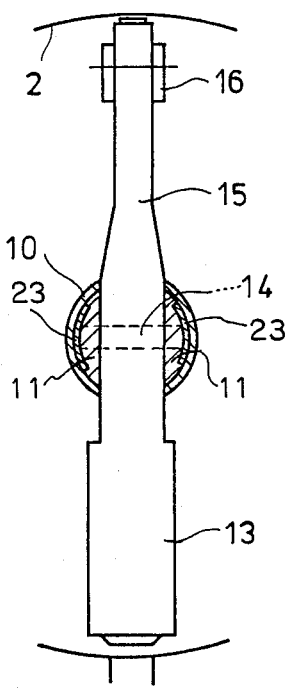
FIG. 3 is a sectional view taken along the line III—III in FIG. 2.
Figure 4:
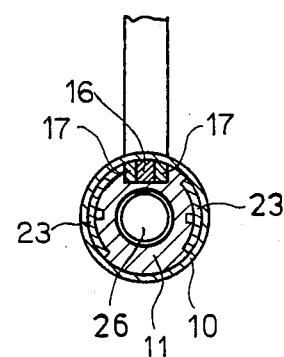
FIG. 4 is a sectional view taken along the line IV—IV in FIG. 2.
Figure 5:
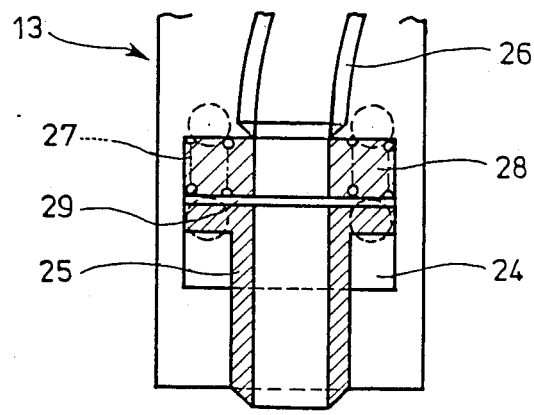
FIG. 5 is an enlarged and detailed view of a portion encircled by the line V in FIG. 2.

Though not shown, the outer guide pipe 10 is equipped at its leading portion with the supporting legs which are selectively diverged or converged by the cylindrical body pushed by the spring and which have the rollers, as is the case with the conventional system as shown in FIG. 2.

The flexible tube 26 receives a supporting cable 45 having at its leading end a spherical body (for instance, a steel ball) 44 having a predetermined weight. An optical fiber 46 extends along the supporting cable 45 and has a leading end extending throught the steel ball 44 and optically coupled to a lens 47 on a frontal peripheral surface of the steel ball 44. An inner diameter $D_1$ of the push flange 37 is slightly greater than an inner diameter $D_2$ of the heat-transfer-tube hole 12 while a diameter $D_3$ of the steel ball 44 is slightly smaller than the inner diameter $D_2$ of the hole 12.

Upon inspection of the wall thickness of the heat-transfer tubes 1, the guide 4 with the above-described construction is inserted through the inspection hole 3 into the header 2 and is supported at its leading portion by the rollers 18 of the supporting legs 9 as shown in FIG. 2.

Next the head 13 is rotated to a vertical position as shown in FIG. 6 and mantained in the position. In this rotation, the leading end of the vinyl tube 26 is curved to be directed toward the heat-transfer-tube hole 12 and the projection 42 is fitted into the groove 41 on the boss portion of the sprocket 40. In this case, the steel ball 44 is located near the inside of the push flange 37 as indicated by the solid lines in FIG. 6.

Thereafter the inspector displaces the guide 4 while watching through the optical fiber 46 for the hole 12 to be inspected and locates the leading end of the flexible tube 26 close to the hole 12. In this case, the position of the hole 12 may be estimated from the inserted length of the guide 4 into the header 2.

After the leading end of the vinyl tube 26 is thus located above the heat-transfer tube hole 12, the supporting cable 45 is loosened to allow the steel ball 44 to drop. In this case, if the tube 26 is not accurately in alignment with the hole 12, the steel ball 44 is caught and prevented from dropping further. Then, the guide 4 is displaced by a small distance to allow the steel ball 44 to drop further. Next the steel ball 44 is raised and dropped for a few times by the supporting cable 45 to confirm the alignment of the leading end of the vinyl tube 26 with the heat-transfer-tube hole 12 from smoothness of the movements. It is to be noted that position of the steel ball 44 can be easily detected by marks placed on the supporting cable 45 extending out of the vinyl tube 26. Alignment accuracy may be suitably set by selecting the inner diameter $D_2$ of the hole 12 and the diameter $D_3$ of the steel ball 44.

After the confirmation of the alignment, the sprocket wheel 40 is rotated by the chain 43 to rotate the threaded shaft 33, whereby the tube guide 35 is lowered to press the push flange 37 against the inner surface of the header 2 to thereby sealingly join the vinyl tube 26 with the hole 12.

Next the steel ball 44 and the optical fiber 46 are pulled out of the vinyl tube 26 by the supporting cable 45. Fluid is applied under pressure to the vinyl tube 26 to deliver the sensor 6 and the floats 7 into the heat-transfer tube 1 so as to inspect the latter. In this case, the correct alignment of the leading end of the vinyl tube 26 with the heat-transfer-tube hole 12 is securely maintained so that leakage of the compressed fluid from the joint can be completely prevented and delivery of the sensor and the like is facilitated.

So far the sprocket wheel and the chain are used respectively as a rolling body and a thread-like member, but a pulley and a rope or belt may be used instead. The sprocket wheel and the threaded shaft may be connected through a universal joint. Instead of the sprocket assembly of the type described above, the leading end of the vinyl tube may be pushed against and joined to the heat-transfer-tube hole by a hydraulic or pneumatic cylinder. The flexible tube may be formed by any suitable material other than vinyl and any suitable materials may be used to fabricate the spherical body, the supporting cable and so on. The spherical body may be solid or hollow, providing that it has a suitable weight. The measuring instrument may be for flaw detection other than measurement of wall-thickness of boiler heat-transfer tubes. Rotatable or unrotatable sensor system may be used. Thus, it is to be understood that various modifications and variations may be made without leaving the scope of the invention.

As described above, according to the nondestructive inspection apparatus for heat-transfer tubes in boilers of the present invention, the leading end of the flexible tube for guiding the measuring instrument through the header into the boiler heat-transfer tube can be easily and positively aligned with the heat-transfer-tube hole so that the vinyl tube is securely pressed against the heat-transfer-tube hole, whereby the inspection can be carried out at a high degree of efficiency while preventing the leakage of the compressed fluid.

What is claimed is:

1. In a non-destructive inspection apparatus for heat-transfer tubes having open ended holes in a header in a boiler, wherein a flexible tube is inserted through an inspection hole into said header and jointed at its leading end to an open ended hole of one of said heat transfer tubes, and a measuring instrument is inserted through said flexible tube into said one heat-transfer tube by a compressed fluid, the improvement comprising means for aligning the leading end of said flexible tube with said open ended hole of said one heat-transfer tube comprising an optical fiber, a supporting cable for inserting said optical fiber into said flexible tube, and a spherical body attached to a leading end of said supporting cable and having an inner diameter slightly smaller than that of said open ended hole of said one heat-transfer tube, a leading end of said optical fiber being disposed at a frontal peripheral surface of said spherical body which faces said open ended hole when the leading end of said flexible tube is in alignment with said open ended hole of said one heat-transfer tube.

2. The apparatus according to claim 1 wherein said spherical body is a steel ball.

3. The apparatus according to claim 1 wherein a push flange is disposed on the leading end of said flexible tube and has a rubber packing on a pressure exerting surface thereof, said push flange being sealingly pressed by pressing means against an inner surface of the header to thereby tightly join the leading end of the flexible tube to the open ended hole of said one heat-transfer tube.

* * * * *